(12) United States Patent
Laquerre et al.

(10) Patent No.: US 6,660,259 B2
(45) Date of Patent: Dec. 9, 2003

(54) HERPES SIMPLEX VIRUS FOR TREATING UNWANTED HYPERPROLIFERATIVE CELL GROWTH

(75) Inventors: Sylvie Laquerre, Walnut Creek, CA (US); Terry Hermiston, Corte Madera, CA (US)

(73) Assignee: Onyx Pharmaceuticals, Inc., Richmond, CA (US)

(*) Notice: Subject to any disclaimer, the term of this patent is extended or adjusted under 35 U.S.C. 154(b) by 0 days.

(21) Appl. No.: 09/733,807

(22) Filed: Dec. 8, 2000

(65) Prior Publication Data

US 2002/0072119 A1 Jun. 13, 2002

Related U.S. Application Data

(60) Provisional application No. 60/169,829, filed on Dec. 8, 1999.

(51) Int. Cl.[7] .................. A01N 63/00; C12P 21/06; C12N 15/66; C12N 15/00; C12N 5/00
(52) U.S. Cl. .................. 424/93.2; 435/320.1; 435/325; 435/91.41; 435/69.1
(58) Field of Search .................. 424/93.2; 435/320.1, 435/325, 91.41, 69.1

(56) References Cited

U.S. PATENT DOCUMENTS

5,804,413 A * 9/1998 DeLuca
6,261,552 B1 * 7/2001 DeLuca
2002/0028195 A1 * 3/2002 Coffey et al.

FOREIGN PATENT DOCUMENTS

WO     WO 92/13943     8/1992

OTHER PUBLICATIONS

Brown et al. The Unique Physiology of Solid Tumors: Opportunities (and Problems) for Cancer Therapy Cancer Research 58. 1408–1416,Apr. 1, 1998.*
Palu et al. In pursuit of new developments for gene therapy of human diseases Journal of Biotechnology 68 1999 1–13.*

* cited by examiner

*Primary Examiner*—James Ketter
*Assistant Examiner*—Konstantina Katcheves
(74) *Attorney, Agent, or Firm*—Gregory Giotta

(57) ABSTRACT

The present invention relates to pharmaceutical compositions, kits, and methods of use thereof, comprising, a mutant human herpes simplex-type 1 virus, which is cytopathic to susceptible hyperproliferative cells, such as neoplastic cells. Preferably, the virus does not produce a fully functionally active wild-type ICP0 polypeptide coded for the IE gene 1.

15 Claims, 4 Drawing Sheets

HERPES SIMPLEX VIRUS FOR TREATING UNWANTED HYPERPROLIFERATIVE CELL GROWTH

This Application claims priority from U.S. Provisional Application No. 60/169,829, filed Dec. 8, 1999.

BACKGROUND OF THE INVENTION

From the early part of this century, viruses have been used to treat cancer. The approach has been two-fold; first, to isolate or generate oncolytic viruses that selectively replicate in and kill neoplastic cells, while sparing normal cells. Here investigators initially used wild type viruses, and this approach met with some, albeit, limited success. While oncolysis and slowing of tumor growth occurred with little or no damage to normal tissue, there was no significant alteration in the course of the disease. See, Smith et al., Cancer 9: 1211–1218 (1956), Cassel, W. A. et al., Cancer 18: 863–868 (1965), Webb, H. E. et al., Lancet 1: 1206–1209 (1966). See, also, Kenney, S and Pagano, J. J. Natl. Cancer Inst., vol. 86, no. 16, p.1185 (1994).

More recently, and because of the reoccurrence of disease associated with the limited efficacy of the use of wild type viruses, investigators have resorted to using recombinant viruses that can be delivered at high doses, and that are replication competent in neoplastic but not normal cells. Such viruses are effective oncolytic agents in their own right, and further, can be engineered to carry and express a transgene that enhances the anti neoplastic activity of the virus. An example of this class of viruses is an adenovirus that is mutant in the E1B region of the viral genome. See, U.S. Pat. No. 5,677,178, and Bischoff, J. R., D. H. Kim, A. Williams, C. Heise, S. Horn, M. Muna, L. Ng, J. A. Nye, A. Sampson-Johannes, A. Fattaey, and F. McCormick. 1996, Science. 274:373–6.

It is important to distinguish the use of replication competent viruses, with or without a transgene for treating cancer, from the second approach that investigators have used to treat cancer, which is a non-replicating virus that expresses a transgene. Here the virus is used merely as a vehicle that delivers a transgene which, directly or indirectly, is responsible for killing neoplastic cells. This approach has been, and continues to be the dominant approach of using viruses to treat cancer. It has, however, met with limited success, and it appears to be less efficacious than replicating viruses.

As mentioned above, to avoid damage to normal tissues resulting from the use of high dose viral therapy it is preferred that the virus have a mutation that facilitates its replication, and hence oncolytic activity in tumor cells, but renders it essentially harmless to normal cells. This approach takes advantage of the observation that many of the cell growth regulatory mechanisms that control normal cell growth are inactivated or lost in neoplastic cells, and that these same growth control mechanisms are inactivated by viruses to facilitate viral replication. Thus, the deletion or inactivation of a viral gene that inactivates a particular normal cell growth control mechanism will prevent the virus from replicating in normal cells, but such viruses will replicate in and kill neoplastic cells that lack the particular growth control mechanism.

The use of genetically engineered replication-competent herpes simplex virus-type 1 (HSV-1) has been reported as an anti-tumor agent. See, Martuza et al., Science 252: 854 (1991). Specifically, it was shown that HSV-1 thymidine kinase-deficient mutant, dlsptk, exhibited anti-tumor activity towards human malignant glioma cells in an animal brain tumor model. Unfortunately, the HSV-1 dlsptk virus produced significant encephalitis at the doses required to kill the tumor cells adequately. See, Markert et al., Neurosurgery 32: 597 (1993).

U.S. Pat. No. 5,585,096 describes a mutated, replication-competent herpes simplex virus-type 1 (HSV-1) which contains mutations in two genes, is sensitive to antiviral agents such as acyclovir, is not neurovirulent and does not replicate in non-dividing cells, yet can kill nervous system tumor cells. This herpes simplex virus mutant is incapable of expressing both a functional gamma 34.5 gene product and ribonucleotide reductase.

U.S. Pat. No. 5,728,379 describes a method for killing tumor cells in vivo with a replication competent herpes simples virus by the regulated expression of an essential immediate-early viral gene product.

U.S. Pat. No. 5,804,413 describes cell lines that express complementing levels of certain herpes simplex virus essential immediate early proteins Although progress has been made in identifying and using viruses for treating disease, particularly cancer, there is obviously still a great need for more effective viruses.

SUMMARY OF THE INVENTION

An aspect of the invention is the description of a method for treating unwanted hyperproliferative cell growth in a cell population with an amount of a mutant herpes simplex virus which is lytic to the cells, wherein the virus does not produce a functionally active wild-type ICP0 polypeptide coded for by the IE gene 1.

Another aspect of the invention is the description of a method for treating neoplastic cells which over express Beta-catenin as compared to normal cells of the same histological type with an effective amount of a mutant human herpes simplex virus, wherein the virus does not produce a functionally active wild-type ICP0 polypeptide coded for by the IE gene 1.

A further aspect of the invention is the description of pharmaceutical compositions consisting of a mutant human herpes simplex virus, wherein the virus does not produce a functionally active wild-type ICP0 polypeptide coded for the IE gene 1.

Another aspect of the invention is a method of identifying cells which overexpress Beta-catenin by administering to the cells an effective amount of a mutant human herpes simplex virus, wherein the virus does not produce a functionally active wild-type ICP0 polypeptide coded for the IE gene 1.

These and other aspects of the invention will become apparent upon a full consideration of the disclosure set forth herein.

DESCRIPTION OF THE INVENTION

Figure 1:
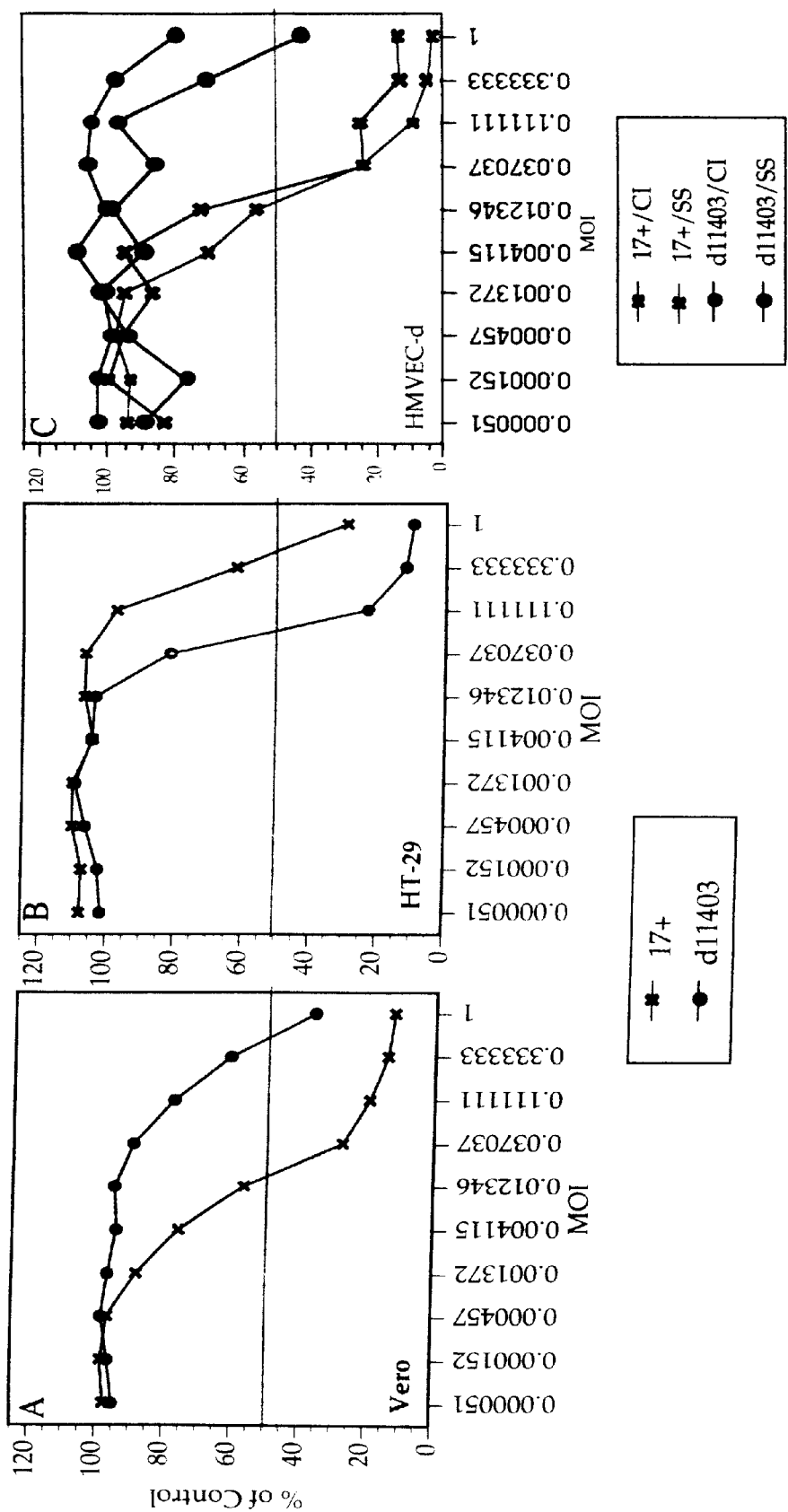
FIG. 1. Comparison of the lytic capacity of wild type 17$^+$ and d11403 on cancer and normal cells. Serial dilution of HSV-1 strain 17$^+$ and its ICP0 deleted derivative (d11403) were used to infect monolayers of transformed Vero (panel A), cancer HT-29 (panel B) and human normal quiescent, HMVEC-d (panel C) cells in a 96 well format. Three (panels A and B) and 6 (panel C) days post infection the plates were processed for MTT assay and read at the optical density of 570 nm. The average of quadruplet virus dilution was plotted as a percentage of uninfected control cell monolayers. The horizontal line marks the moi of 50% cell death.

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., *Molecular Cloning: A Laboratory Manual*, 2nd. *edition* (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

The term "hyperproliferative cell growth" or "hyperproliferative cell" refers to a disease state characterized by an abnormal or pathological proliferation of cells, for example, neoplasia.

As used herein, "neoplastic cells" and "neoplasia" refer to cells which exhibit relatively autonomous growth, so that they exhibit an aberrant growth phenotype characterized by a significant loss of control of cell proliferation. Neoplastic cells comprise cells which may be actively replicating or in a temporary non-replicative resting state ($G_1$ or $G_0$); similarly, neoplastic cells may comprise cells which have a well-differentiated phenotype, a poorly differentiated phenotype, or a mixture of both type of cells. Thus, not all neoplastic cells are necessarily replicating cells at a given timepoint. The set defined as neoplastic cells consists of cells in benign neoplasms and cells in malignant (or frank) neoplasms. Frankly neoplastic cells are frequently referred to as tumor cells or cancer cells, typically termed carcinoma if originating from cells of endodermal or ectodermal histological origin, or sarcoma if originating from cell types derived from mesoderm.

The term "cytopathic" encompasses any pathological or deleterious effect on a hyperproliferative cell caused by the invention herpes virus, including, lysis, apoptosis, arrest of cell growth, arrest of cell reproduction, arrest of the cell-cycle, destruction of vital organelles, such as mitochondria, nuclei, and cell membranes, DNA fragmentation, cytoplasmic blebbing, etc As used herein, "physiological conditions" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl (or optionally KCl), pH 6.5–8.1, and a temperature of approximately 20–45° C. Generally, physiological conditions are suitable binding conditions for intermolecular association of biological macromolecules. For example, physiological conditions of 150 mM NaCl, pH 7.4, at 37° C. are generally suitable.

The present invention relates to herpes simplex viruses type 1 (HSV-1) which comprise mutations in at least one immediate early gene of the HSV-1 genome. These viruses are able to infect, and are cytopathic to hyperproliferative cells, making them useful as therapeutic, and diagnostic agents for treating or diagnosing certain diseases. In preferred embodiments, the viruses are selectively cytopathic to a specific cell type in a mixed population of cells, a hyperproliferative cell, thereby facilitating its selective elimination from the total cell population. This property of the virus is especially advantageous since it treats diseased cells, without significant deleterious effects on normal cells. The hyperproliferative cells are preferably transformed or neoplastic cells, or other cells exhibiting hyperproliferative cell growth. Thus, for example, the viruses are useful in treating neoplasia, preferably by causing the neoplastic cells, but not normal cells, to undergo oncolysis or other cytopathic effects. Cells which overexpress the Beta-catenin polypeptide are especially susceptible to the cytopathic and/or lytic effect of viruses according to the present invention. As a result, the viruses are preferably useful for treating neoplastic cells which are defective in Beta-catenin metabolism, and also for detecting such defects.

A preferred embodiment of the invention relates to a method for treatment or prophylaxis of a neoplasm by administering to the neoplasm an amount of a mutant human herpes simplex virus which is cytopathic and/or lytic to cells, where the virus does not produce a fully functionally active wild-type ICP0 polypeptide coded for by the IE gene 1.

The present invention also relates to methods of identifying cells which over express Beta-catenin, comprising one or more of the following steps in any effective order, e.g., administering to said cells an effective amount of a mutant human herpes simplex virus, wherein said virus does not produce a fully functionally active wild-type ICP0 polypeptide coded for by the IE gene 1, and determining the occurrence of a cytopathic effect and/or lysis in said cells, whereby said cells are identified as over expressing Beta-catenin.

Any neoplasm can be treated with the viruses as long as it susceptible to its cytopathic/lytic, effect. Whether a neoplasm is susceptible to the viral effect can be determined routinely, e.g., as shown in the examples below. For instance, cells from either a primary or established cell line can be placed in an in vitro culture and contacted with varying amounts of virus (e.g., serial dilutions). Several days after infection, the cells can be assayed for viability and/or cell death to determine whether lysis has occurred. Viability and/or cell death assays can be accomplished routinely, e.g., by MTT assay as described by Promega Corporation using its commercial kit, Cell Titer 96™. See also, Komeniewski, C. and Callewaert, D. M. (1983) J. Immunol. Methods 64, 313, and Decker, T. and Lohmann-Matthes, M.-L (1988) J. Immunol. Methods 115, 61. As shown in the examples, colon cancer cells (including colorectal cancer, colon adenocarcinoma, etc.) are preferred targets of the virus since they are especially susceptible to the viral lytic effect. Other neoplasms that can be treated include, but are not limited to, neoplasms of prostate, lung, stomach, breast, uterus, ovary, pancreas, bladder, kidney, brain, bone, blood, oropharyngeal, head and neck, esophagus, testis, cervix, thyroid, adrenal gland, lymphoma, melanoma, leukemia, myeloma, Hodgkins, carcinoma, choriocarcinoma, sarcoma, neuroblastoma, Wilms disease, benign tumors, and precancerous cells.

Hyperproliferative cells, for example neoplastic cells, for reasons not understood, are the preferred targets of the invention herpes viruses if they express amounts of the polypeptide Beta-catenin in excess of normal amounts for that particular cell type. By the term "over expression as" used herein, it is meant that the levels of Beta-catenin in a diseased target cell are higher, e.g., 10%, 20%, 40%, 50%, 70%, 90%, 95%, 99%, 100%, 200%, than those in a normal cell of the same type. Beta-catenin is a polypeptide involved in cell adhesion and signal transduction. It has been shown herein that susceptibility to the lytic effect of the IE-1 gene mutations is correlated with the expression levels of Beta-catenin. Cells which express high levels of the polypeptide were most susceptible to the lytic effect, while cells express moderate levels were moderately susceptible to lysis. Thus, whether a neoplastic cell will be susceptible to a virus in accordance with the present invention can be determined routinely by measuring its expression levels of Beta-catenin. Conversely, viral susceptibility can be used to determine whether a cell is overexpressing the polypeptide, a mutant thereof. This is not to exclude cells susceptible to virus but which do not overexpress Beta-catenin Cells which are defective in Beta-catenin metabolism can also be treated in accordance with the present invention. By "defective metabolism," it is meant any cellular mechanism that leads to the abnormal expression of the Beta-catenin polypeptide, preferably overexpression as described above. For example, mutations in the Beta-catenin gene, and in genes that modulate its expression, can result in its excessive expression. Specific mutations in Beta-catenin have been identified in human tumors. These mutations prevent the down-regulation of Beta-catenin by APC. See, e.g., Rubinfeld et al., Science, 275:1790–1792, 1997; Morin et al., Science, 275:1787–1790, 1997. Beta-catenin can also be oncogenically activated by the inactivation of the APC tumor suppressor, or by activation of the wnt-1 signaling pathway; both modulate Beta-catenin. All three of these mechanisms result in the overexpression of Beta-catenin polypeptide. See, e.g., Polakis, Curr. Opinion Genet. Dev., 9:15–21, 1999. Thus, the present invention can be used to treat cells comprising one or more mutations in the Beta-catenin, wnt-1, and APC genes, which mutations result in excessive Beta-catenin levels. Viruses which are useful in the present invention preferably have a mutation in an immediate early (IE) gene, such as nonessential IE genes, including ICP0, ICP22, ICP47, ORF-P, ORF-0, and US1.5, while essential genes include ICP4 and ICP27.

A preferred gene is a IE gene 1 (IE-1) which codes for the Vmw110 or ICP0 polypeptide. It is a phospho-nuclear protein of 775 amino acid residues with an apparent Mr 110 K (Perry et al., J. Gen. Virol., 67:2365–2380, 1986). It is present in 2 copies within the HSV genome but yet is not absolutely required for the in vitro lytic infection.

In preferred embodiments of the invention, the ICP0 polypeptide is not a functionally-active wild-type ICP0 polypeptide. By the phrase "not a functionally-active wild-type polypeptide," it is meant that polypeptide is substantially deficient in at least one biological activity that a normal (wild-type) polypeptide displays. It is recognized that in some circumstances the IE-1 gene product may exhibit some residual amount of activity, but still possess its lytic effect. Thus, the present invention includes mutant HSV-1 IE-1 mutants which are cytopathically/lytically effective but exhibit less ICP0 activity than a wild-type virus, e.g., 50%, 75%, 90%, 95%, 99% less, etc.

ICP0 displays a number of biological activities in various in vivo and in vitro processes, including, but not limited to, activating viral gene expression during lytic infection; reactivating virus from latency; associating with nuclear structures known as ND10, promyelocytic leukaemia bodies or PODS; associating with centromeres in both mitotic and interphase cells; binding to DNA in crude extracts; associating with chromatin in infected nuclei; binding to a 135 kDa cellular protein (Herpes Associated Ubiquitin Specific Protease, HAUSP, (Meredith et al., Virology, 200:457–469, 1994); interacting with cyclin D3 (Kawaguchi et al., J. Virol., 71:7328–36, 1997; Van Sant, Proc. Natl. Acad. Sci., 96:8184–8189, 1999) and EF1-Delta (Kawaguchi, J. Virol. 71:1019–1024, 1997). Its deletion results in a multiplicity-dependent lytic infection that markedly reduces the probability of an ICP0 mutant initiating a productive infection (Stow, J. Gen. Virol., 67(pt12):2571–2585, 1986; Sacks, J. Virol., 61:829839, 1987). See, also, e.g., Everett, J. Mol. Bio., 202:87–96, 1988; Everett et al., EMBO Journal, 18:1526–1538, 1999. A preferred activity is its ability to transactivate transcription from co-expressed promoters. Assays can be carried out as described in, e.g., Everett, J. Gen. Virol., 70:1185–1202, 1989; Everett, J. Mol. Bio., 202:87–96, 1988. For instance, a plasmid expressing a mutant ICP0 can be co-expressed with a plasmid comprising a promoter coupled to a detectable marker, where the promoter can be gD, pSV37/30, SVgD, SV40, etc. The plasmids can be co-transfected and co-expressed in various cell lines, including, BHK, Vero, 293, A549, HeLa, WSHeLa, etc.

The choice of the cell line and promoter sequence can be determined conventionally, e.g., Everett, J. Mol. Bio., 203:739–751, 1988 and O'Hare and Hayward, J. Virol, 56:723–733, 1985. Typically, the promoter can be operably linked to a coding sequence which codes for a detectable product (e.g., chloramphenicol acetyl transferase). DNA regions are operably linked when they are functionally related to each other. For example, a promoter is operably linked to a coding sequence if it controls the transcription of the sequence. A promoter, or other expression control sequences (including, enhancers, ribosome binding sites, RNA polymerase binding sites, etc.) is operably linked to a nucleotide coding sequence when the promoter sequence is positioned in such a manner to effect or achieve expression of the coding sequence. For example, when a promoter is operably linked 5' to a coding sequence, expression of the coding sequence is driven by the promoter. Transactivation of the promoter sequence by ICP0 results in expression of the detectable product, providing a signal that the ICP0 polypeptide is functionally-active. ICP0 acts synergistically with the IE-3 gene product, Vmw175. Thus, the ability of a mutant HSV-1 IE-1 to transactivate a promoter can be measured in the presence and absence of Vmw175. See, e.g., Everett, J. Mol. Bio., 202:87–96, 1988. The term "transactivation," as used herein refers to the activation of gene sequences by factors encoded by a regulatory gene, such as IE-1, which is not necessarily contiguous with the gene sequences to which it binds and activates.

A preferred mutant virus in accordance with the present invention as mentioned is one substantially deficient in a fully functionally active wild-type ICP0 polypeptide coded for by the IE-1 gene. Functional inactivation of the gene can be accomplished in any manner which is effective to knock out (i.e., eliminate) one or more functions of the IE-1 gene. For example, the wild-type IE-1 gene can be modified by deleting or inserting sequence into it. A preferred deletion is dl1403 which is described in Stow, J. Gen. Virol, 67:2571–2585, 1986; Perry et al., J. Gen. Virol., 67:2365–2380, 1986. Other mutations, and methods of making them, are described in, e.g., Everett, J. Mol. Bio., 202:87–96, 1988, especially Tables 1 and 2, or any mutation that decreases or abolishes one or more of the multiple functions of ICP0.

A virus in accordance with the present invention can further comprise other modifications in its genome. For example, it can comprise additional DNA inserted into the IE-1 gene. This insertion can produce functional inactivation of the IE-1 gene and the resulting lytic phenotype, or it may be inserted into an already inactivated gene, or substituted for a deleted gene.

Any desired DNA can be inserted, including DNA that encodes selectable markers, or preferably genes coding for a therapeutic, biologically active protein, such as interferons, cytokines, chemokines, or more preferably DNA coding for a prodrug converting enzyme, including thymidine kinase (Martuza et al., *Science,* 252:854, 1991), cytosine deamindase (U.S. Pat. No. 5,358,866), cyp450 (U.S. Pat. No. 5,688,773), and others.

Other examples of genes that encode therapeutically or biologically active proteins, or fragments thereof, include those that encode immunomodulatory proteins such as, by way of example, interleukin 2 (U.S. Pat. Nos. 4,738,927 or 5,641,665); interleukin 7 (U.S. Pat. Nos. 4,965,195 or 5,328, 988); interleukin 12 (U.S. Pat. No. 5,457,038); tumor necrosis factor alpha (U.S. Pat. Nos. 4,677,063 or 5,773,582); interferon gamma (U.S. Pat. Nos. 4,727,138 or 4,762,791); or GM-CSF (U.S. Pat. Nos. 5,393,870 or 5,391,485). Additional immunomodulatory proteins further include macrophage inflammatory proteins, including MIP-3, (See, Well, T. N. and Peitsch, MC. J. Leukoc. Biol vol 61 (5): pages 545–50,1997), and cell suicide, or apoptosis inducing proteins, including BAD and BAX. See, Yang, E., et al. Cell, vol 80, pages 285–291 (1995); and Sandeep, R., et al Cell, vol. 91, pages 231–241 (1997). Monocyte chemotatic protein (MCP-3 alpha) may also be used. A preferred embodiment gene is a chimeric gene consisting of a gene that encodes a protein that traverses cell membranes, for example, VP22 or TAT, fused to a gene that encodes a protein that is preferably toxic to neoplastic but not normal cells.

Additionally, a herpes virus in accordance with the present invention can comprise mutations at other positions in its genome, in addition to IE-1.

Herpes virus in accordance with the present invention is administered in any way suitable to achieve the desired effect i.e., it is administered under effective conditions. In a preferred embodiment, the virus is administered to treat a neoplasm. The virus is generally administered in an amount that is effective to produce a cytopathic effect in the neoplastic cells, e.g., in an amount which is lytic or oncolytic to the cells. By the terms "lytic" or "oncolytic," it is meant that the virus produces disintegration (lysis) in hyperproliferative target (e.g., neoplastic) cells preferentially over normal cells. Thus, the virus is cytopathic to such cells.

Effective amounts to accomplish lysis, tumor regression, or other therapeutic effects can be determined routinely, e.g., by performing a dose-response experiment in which varying doses are administered to target cells to determine an effective amount in producing lysis. Amounts are selected based on various factors, including the milieu to which the virus is administered (e.g., a patient with cancer, animal model, tissue culture cells, etc.), the site of the cells to be treated, the age, health, gender, and weight of a patient or animal to be treated, etc. Useful amounts include, e.g., $10^5$–$10^{12}$ pfus, preferably, $10^7$–$10^8$ pfus.

The mutant HSV viruses described herein preferably are cytopathic or lytic to neoplastic cells. Thus, it is preferred that a treatment in accordance with the invention results in lysis of the neoplastic cells. In this sense, treatment indicates that the disease is altered by eliminating neoplastic cells. Such elimination can result in tumor regression. However, treatment can also cause the tumor to stop or slow growth, without any noticeable regression. In a preferred method of the present invention, a virus is used to eliminate by lysing neoplastic cells from normal population, in a host (e.g., a human with neoplasia or a nonhuman mammal comprising a graft of neoplastic cells, such as human neoplastic cells injected subcutaneously or intraperitaneally as in an animal model).

The virus can be administered by any means suitable to achieve a therapeutic effect, for example, by injection directly into, or close by, a tumor, intratumorally, topically, enterally, parenterally, intravenously, intramuscularly, subcutaneously, orally, nasally, intracerebrally, intraventricularly, depending upon the location of the hyperproliferative target cells.

The invention herpes virus can be administered as naked DNA, as a virus particle, in liposomes, complexed to a suitable carrier, such as calcium phosphate, DEAE-dextran complexes, lipids, polymers, etc. See, e.g., U.S. Pat. No. 5,976,567 and 5,962,429. The virus can be produced conventionally in culture and packaged into a mature viral particle, or the naked DNA can be prepared and complexed to any suitable carrier, such as those mentioned above. A herpes virus in accordance with the present invention can be administered with any other therapy useful to treat a neoplasm, or other hyperproliferative cell growth. Including, e.g., surgery, radiation, and chemotherapeutic agents, such as alkylating agents (e.g., cisplatin), structural analogs or antimetabolites (e.g., methotrexate), hormonal agents (e.g., tamoxifen), androcorticosteroids (e.g., prednisone), aromatase inhibitors, GnRH analogs, biologic response modifiers (e.g., interferons), peptide hormone inhibitors, natural products (e.g., vinblastine, mitomycin), etc. See, e.g., *Current Medical Diagnosis and Treatment,* Tierney et al., ed., 1997, Pages, 81–87.

A pharmaceutically acceptable carrier or excipient may be used to deliver the virus. A variety of aqueous solutions can be used, eg., water, buffered water, 0.4% saline, 0.3% glycine proteins and the like. These solutions are sterile and generally free of particulate matter other than the desired herpes viral vector. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance infection of cells by herpes virus may be included.

Chemotherapy may be administered by methods well known to the skilled practitioner, including systemically, direct injection into the cancer, or by localization at the site of the cancer by associating the desired chemotherapeutic agent with an appropriate slow release material or intraarterial perfusing the tumor. The preferred chemotherapeutic agent is cisplatin, and the preferred dose may be chosen by the practitioner based on the nature of the cancer to be treated, and other factors routinely considered in administering cisplatin. Preferably, cisplatin will be administered intravenously at a dose of 50–120 mg/m$^2$ over 3–6 hours. More preferably it is administered intravenously at a dose of 80 mg/m$^2$ over 4 hours. A second chemotherapeutic agent, which is preferably administered in combination with cisplatin is 5-fluorouracil. The preferred dose of 5-fluorouracil is 800–1200 mg/m$^2$ per day for 5 consecutive days.

The present invention also relates to pharmaceutical compositions comprising an effective amount of an invention herpes virus in accordance with the present invention, e.g., where the virus is in a form for therapeutic use. In addition, the invention relates to kits comprising a mutant human herpes simplex virus which is lytic to cells in said neoplasm, wherein said virus does not produce a functionally active wild-type ICP0 polypeptide coded for the IE gene 1 and a chemotherapeutic agent, such as those mentioned above.

The following examples are presented to illustrate the present invention and to assist one of ordinary skill in making and using the same. The examples are not intended in any way to otherwise limit the scope of the disclosure or the protection granted by Letters patent hereon.

EXAMPLES

The HSV immediate early protein ICP0 has been reported to be non-essential for the productive infection (Stow, *J.*

Gen. Virol., 67(pt12):2571–2585, 1986, and shown in FIG. 1A). Analysis of the ICP0 virus dl1403 on a primary normal cells (Human microvascular epithelial cells, dermal origin, HMVEC-d, FIG. 1C) showed marked attenuation (approx 50×) of the viral infection relative to the wild type ($17^+$).

Figure 2:
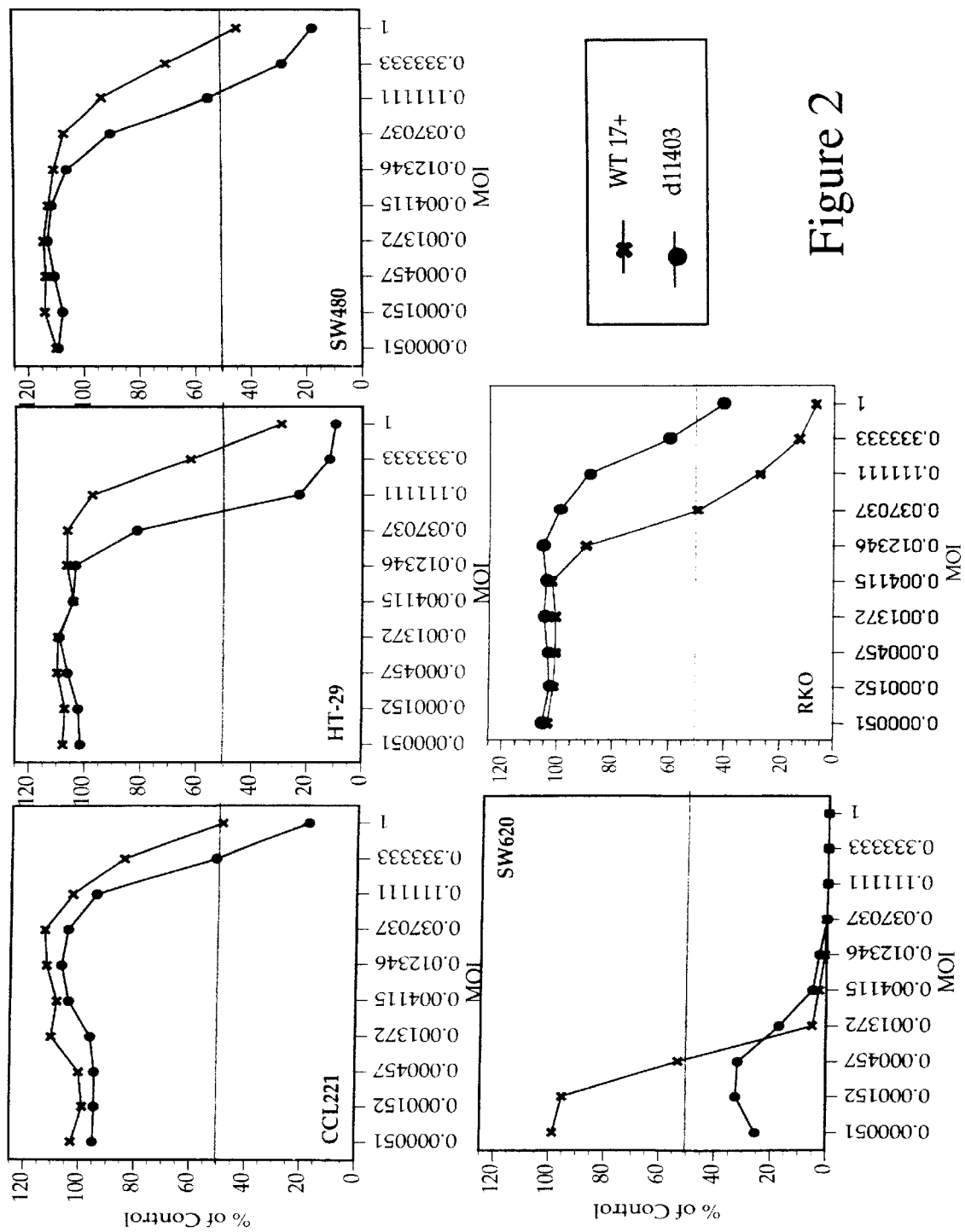
FIG. 2. Comparison of the lytic capacity of wild type 17$^+$ and d11403 on colon cancer cells. Serial dilution of HSV-1 strain 17$^+$ and its ICP0 deleted derivative (d11403) were used to infect monolayers of colon cancer cell lines in a 96 well format. Three days post infection an MTT assay was performed and the average of quadruplet virus dilution was plotted as a percentage of uninfected control cell monolayers. The horizontal line marks the moi of 50% cell death.

Oncolytic analysis of dl1403 virus on several cell lines demonstrated that this virus was generally attenuated compared to wild-type virus except on colon cancer cell lines (FIG. 2). However, the lytic capacity of this deleted virus was better than wt $17^+$ on the colon cancer cell line HT-29 (FIG. 1B).

The dl1403 oncolytic capacity on colon cancer cell lines tested corresponded to the cellular level of Beta-catenin (FIG. 2). For example, SW620 which expresses high level of Beta-catenin was most susceptible to dl1403 lysis. CCL221, HT-29 and SW480 which express moderate levels of Beta-catenin were moderately susceptible to dl1403 compared to $17^+$, while RKO with lower to normal levels of Beta-catenin is most refractory to dl1403 lysis relative to $17^+$ (level of Beta-catenin determined in previous studies, e.g., Polakis, P. Biochim Biophys Acta. Vol. 7: p. 1332 (3), 1997; and Polakis, P. Curr. Opin. Genet Dev. Vol. 9 (1): p. 15 1999). Consequently, if the attenuation of dl1403 compared to $17^+$ on normal cell lines, (50×relative to $17^+$) were coupled with the increased potency of this virus on colon cancer cell lines (10×relative to $17^+$), the in vitro therapeutic index of dl1403 compared to $17^+$ for colon cancer cells goes to 500 fold.

Figure 3A:
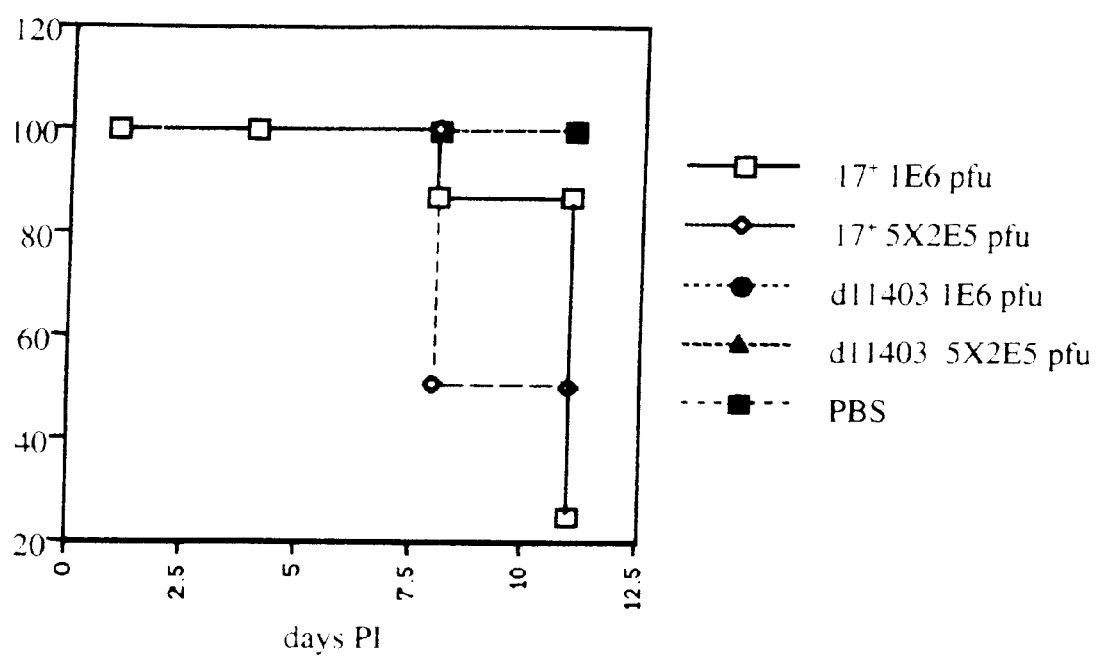
FIG. 3. In vivo analysis of wild type 17$^+$ and d11403 viruses. Wild-type 17$^+$ and d11403 viruses were intratumorally injected in SW620 tumor xenograft in nude mice at $1\times10^6$ pfu once or at $2\times1^{50}$ pfu daily for five days. Animal survival (panel A) as well as tumor sizes (panel B) were monitored.
Figure 3B:
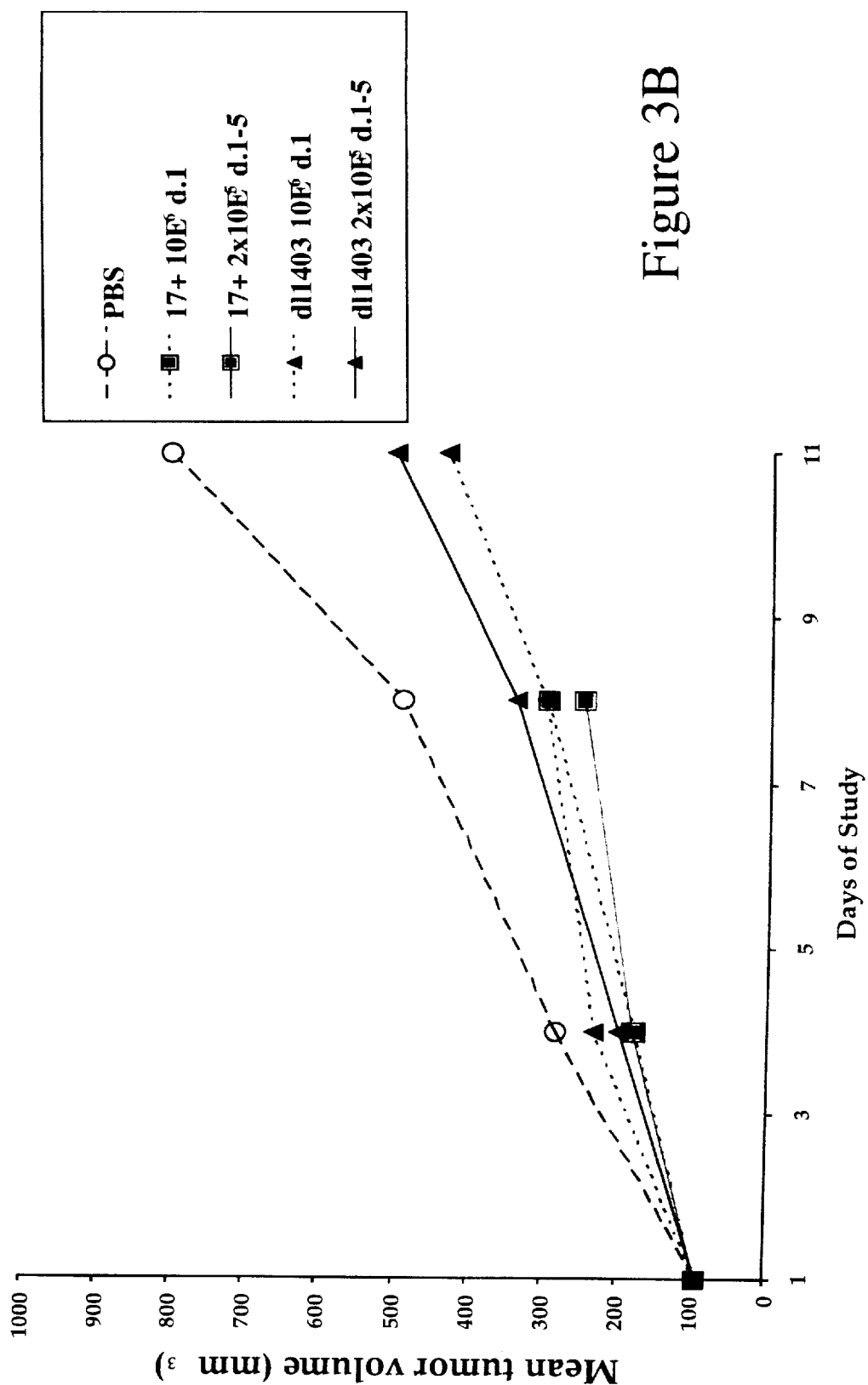

Further, animal studies have demonstrated that a single dose (1×106 pfi) of $17^+$ injected intratumorally into SW620 derived xenograft tumors on nude mice caused animal mortality (20% death 11 day post infection, (PI), FIG. 3A). In contrast, a similar dose of dl1430 is well tolerated in the animals (100% survival) (FIG. 3A) and, in addition, produced a 50% tumor reduction compared to untreated animals (FIG. 3B).

For other aspects of the cell culture, virology, nucleic acids, polypeptides, etc., reference is made to standard textbooks. See, e.g., Davis et al. (1986), *Basic Methods in Molecular Biology*, Elsevir Sciences Publishing, Inc., New York; Hames et al. (1985), *Nucleic Acid Hybridization*, IL Press, *Molecular Cloning*, Sambrook et al.; *Current Protocols in Molecular Biology*, Edited by F. M. Ausubel et al., John Wiley & Sons, Inc; *Current Protocols in Protein Science;* Edited by John E. Coligan et al., John Wiley & Sons, Inc.; *Animal Cell Culture,* Freshney et al., IRL Press, 1992; *Basic Cell Culture Protocols,* Pollard and Walker, Humana Press, 1997; *General Techniques of Cell Culture,* Harrison and Rae, Cambridge University Press, 1997; *Virus Culture,* Cann, ed., Oxford University Press, 1999; *Herpes simplex Virus Protocols,* Brown and MacLean, eds., Humana Press, 1998.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all patents and publications, cited above and in the figures are hereby incorporated in their entirety by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for treating a tumor in a cell population with a herpes simplex virus comprising neoplastic cells defective in beta-catenin metabolism, comprising: injecting said tumor with an amount of a mutant herpes simplex virus which is lytic to said cells, wherein said virus does not produce a functionally active wild-type ICP0 polypeptide coded for by the herpes simplex virus IE 1 gene 1, thereby allowing said virus to lysis said neoplastic cells.

2. A method of claim 1, wherein said virus comprises a deletion in the IE gene 1.

3. A method of claim 2, wherein said deletion is in region 1, 2, 3, 4, or 5 of IE gene 1.

4. A method of claim 1, wherein the virus is dl1403.

5. A method of claim 1, wherein said virus comprises an insertion in the IE gene 1.

6. A method of claim 1, wherein said ICP0 polypeptide has no detectable activity in a transfection assay.

7. A method of claim 1, wherein said cells are neoplastic cells and said cells overexpress Beta-catenin as compared to normal cells of the same type.

8. A method of claim 1, wherein said cells comprise a mutation in the APC gene.

9. A method of claim 7, wherein said cells comprise a mutation in the APC gene.

10. A method of a claim 1, wherein said cells comprise a mutation in the wnt-1gene.

11. A method of claim 7, wherein said cells comprise a mutation in the wnt-1gene.

12. A method of claim 1, wherein said cells comprises mutation in the Beta-catenin gene.

13. A method of claim 7, wherein said neoplastic cells comprise a mutation in the Beta-catenin gene.

14. A method of claim 7, wherein said neoplastic cells are selected from the group consisting of colon, colorectal, or adenocarcinoma.

15. A method as described in claim 1, further comprising determining an effective dose of said mutant herpes simplex virus for treating said neoplastic cell growth, comprising performing a dose-response experiment in which varying doses of said virus are administered to said neoplastic cells to determine an effective amount of virus, said varying doses ranging from $10^5$–$10^{12}$ pfus.

* * * * *